(12) United States Patent
Orikasa et al.

(10) Patent No.: US 6,241,516 B1
(45) Date of Patent: Jun. 5, 2001

(54) ORTHODONTIC DEVICE

(75) Inventors: Masaaki Orikasa; Yasushi Watanabe, both of Fukushima (JP)

(73) Assignee: Tomy Incorporated, Fukishima (JP)

( * ) Notice: Subject to any disclaimer, the term of this patent is extended or adjusted under 35 U.S.C. 154(b) by 0 days.

(21) Appl. No.: 09/361,130

(22) Filed: Jul. 27, 1999

(30) Foreign Application Priority Data

Jul. 28, 1998 (JP) .................................................. 10-212141

(51) Int. Cl.[7] ........................................................ A61C 3/00
(52) U.S. Cl. .................................................. 433/17; 433/23
(58) Field of Search ................................ 433/17, 23, 8

(56) References Cited

U.S. PATENT DOCUMENTS 3,335,496 * 8/1967 Andrews et al. ...................... 433/17
4,386,908 * 6/1983 Kurz .......................................... 433/9
5,529,491 * 6/1996 Hilgenfeldt et al. .................... 433/23

* cited by examiner

Primary Examiner—John J. Wilson
Assistant Examiner—Melba Bumgarner
(74) Attorney, Agent, or Firm—Kenyon & Kenyon

(57) ABSTRACT

In an orthodontic device, a main body (1) has an opening (1a) formed to permit detachable passage of a principal wire and a flange (2) formed in a mesiodistal direction so that the device is fixed via said extension flange (2) to an band to be fitted over the crown of molar. The width (W) of the extension flange (2) in an occluso-gingival direction is made greater than the width (B) of said main body (1) in the same direction.

17 Claims, 7 Drawing Sheets

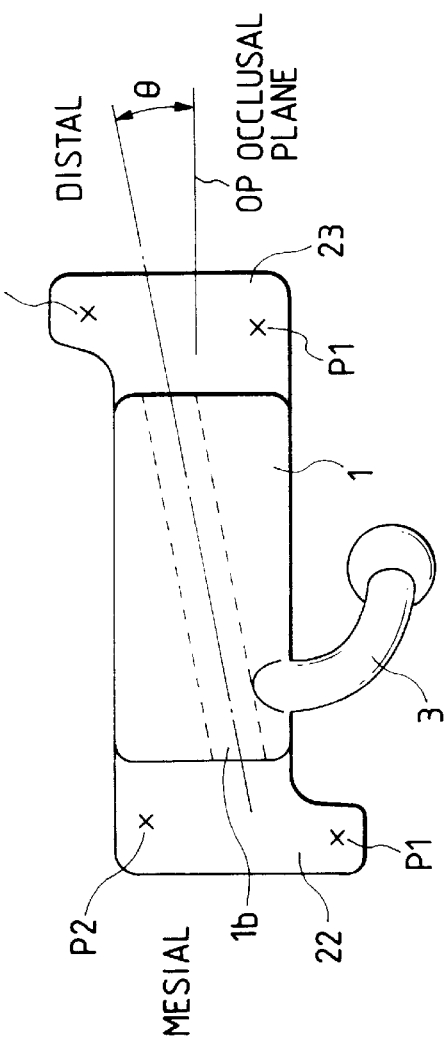
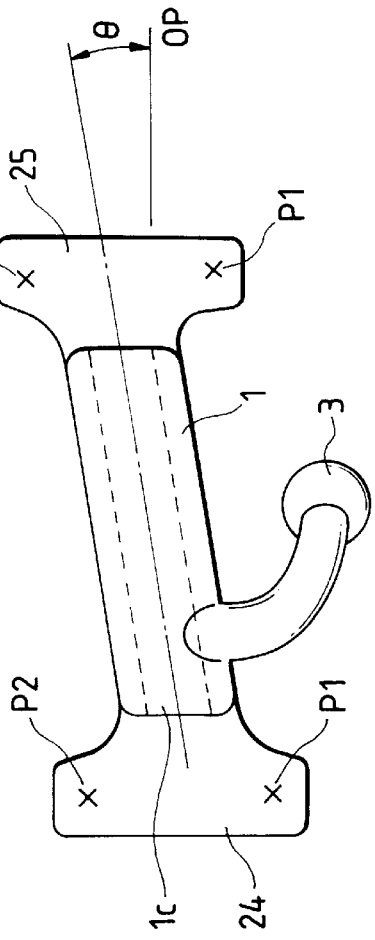
FIG. 7A  FIG. 7B  FIG. 8A  FIG. 8B

ORTHODONTIC DEVICE

BACKGROUND OF THE INVENTION

1. Field of Invention

The present invention relates an improvement of an orthodontic device in the orthodontic treatment, specifically, to an orthodontic device, which is welded to a band, such as a buccal tube, a lingual sheath, a lingual tube and the like.

2. Description of the Related Art

For orthodontic treatment, brackets retaining an arch wire are fixed on the surfaces of the patient's teeth and the elastic recovery of the arch wire is applied to the teeth via the bracket. The bracket is used with a buccal tube which is fitted over the molars of the patient with the aid of a band and its principal purpose is to retain the ends of the arch wire. As shown in FIGS. 3A and 3B, the buccal tube has a broad weld flange 12. A rectangular tube body 11 and a hook 13 are brazed to the top surface of the broad weld flange 12. The tube body 11 has a through-hole 11a through which an end of the arch wire is detachably passed in a mesiodistal direction. The hook 13 is used to engage an elastic ring or a ligature wire.

With this construction, the buccal tube has the advantage that it can be readily welded in position to the band by virtue of the broad weld flange 12. On the other hand, in order to make the buccal tube, separate components have to be assembled by brazing and this not only lowers the efficiency of construction but also causes the disadvantage that the materials of the respective components may be embrittled by the heat of brazing. Moreover, brazing the rectangular tube body 11 to the top surface of the weld flange 12 results in the addition of the thickness of the flange 12 to the thickness of the bottom of the rectangular tube body 11 which defines the IN and OUT or prominence over the tooth enamel. Consequently, this makes it impossible to adjust the value of IN/OUT H to 0.3 mm according to the orthodontist's requirement. In a typical case where the bottom of the rectangular tube body 11 has a thickness of 0.5 mm and the flange 12 has a thickness of 0.3 mm, the value of H is 0.8 mm.

Under the circumstances, a compact, integrally molded buccal tube of the type shown in FIGS. 4A and 4B has recently been proposed. Since this buccal tube is molded as an integral unit (one-piece unit), it has the major advantage of eliminating the cumbersome assembling operation. In addition, it has the advantage of providing great latitude in meeting the orthodontist's requirement for H=0.3 mm. On the other hand, the width of the weld flange 12 in an occluso-gingival direction is adapted to be the same as the width of the rectangular tube body 11 in the same direction and this presents a serious problem when the flange 12 is welded to the band.

FIG. 5 shows how the buccal tube is welded to the band 14. A pair of electrodes 15 in a spot welding machine are used to fix the weld flange 12 to the buccal surface of the band 14. Needless to say, great difficulty is encountered with the welding procedure if the weld flange 12 is narrow. Particularly, due to the pressure applied during electric heating, the weld flange 12 fuses to become disfigured, and as shown in FIG. 6, pressure marks 16 are formed as concave portions and dusts 17 flown due to welding accidentally clog the entrance (exit) of the through-hole 11a, potentially making it impossible for an end of the arch wire to be passed through the hole 11a in the rectangular tube body 11.

A method that could solve the aforementioned problem with the buccal tube of an integral molding type (so-called as a one-piece type) is to increase the length of the weld flange 12 as much as possible in a mesiodistal direction. If the weld flange 12 is elongated in a mesiodistal direction, because this flange 12 curves toward the lingual side, it can be welded in positions far from the entrance and exit of the through-hole 11a in the rectangular tube body 11, thus eliminating the possibility of the disfigured flange or pressure marks to clog the entrance and exit of the through-hole 11a.

This method is effective in preventing the clogging of the entrance and exit of the through-hole 11a. However, if the weld flange 12 is unduly long, the buccal tube no longer conforms to the shape of the band 14. Finally, the band 14 may be deformed upon welding and eventually fails to fit to the crowns of corresponding molars.

A second method that could be applied is to broaden the rectangular tube body 11 as well as the weld flange 12 in an occluso-gingival direction. Given the same size of the through-hole 11a, the rectangular tube body 11 that is broadened together with the weld flange 12 also allows for the weld flange 12 to be welded in such positions that do not interfere with the entrance or exit of the through-hole 11a.

The second method is also free from the problem of blocking the entrance and exit of the through-hole 11a. However, if the rectangular tube body 11 is broadened together with the weld flange 12, it may then have occlusive interference with antagonistic teeth on the occlusion side or it may contact the gingiva on the gingival side to cause its potential swelling. As a further problem, brushing is difficult to perform and this is not desirable to oral hygiene. In addition, the usual practice in the second method is to make the top side (buccal side) of the rectangular tube body 11 round enough to relieve the discomfort that may be felt by the patient after being equipped with the buccal tube. However, the mold to make the rectangular tube body 11 is of such a construction that the position in which the hook 13 is formed lowers in a direction toward the buccal side to increase the chance of the hook 13 of contacting or burying in the gingiva. Further, food debris remaining under the hook 13 is difficult to brush off, again causing a problem in oral hygiene.

SUMMARY OF THE INVENTION

It is an object of the present invention to provide an orthodontic device which, in the case of being welded to a band, is free from the possibility that the entrance and exit of the opening through which a principal wire is to be passed are blocked.

The present invention has been accomplished under these circumstances of the conventional orthodontic devices. According to a first aspect of the present invention, an orthodontic device comprises a main body having an opening formed to permit detachable passage of a principal wire and a flange to extend in a mesiodistal direction such that the device is fixed via said extension flange to a band to be fitted over a teeth, wherein the width of the extension flange in an occluso-gingival direction is greater than the width of said main body in the same direction.

According to a second aspect of the present invention which is a modification of the first aspect, the positions in which the extension flange is to be fixed to the band are away from the boundary of the opening through which a principal wire is to be passed and displaced toward both the occlusal and gingival side.

According to a third aspect of the present invention which is a modification of the first or second aspect, the width of the main body in an occluso-gingival direction is small enough to avoid not only the occlusive interference with antagonistic teeth on the occlusion side but also the contact with the gingiva on the gingival side.

According to a fourth aspect of the present invention which is a modification of any one of the first to third aspects, hook lies on a ridgeline on both the gingival and buccal sides of the main body and extends in a direction toward the gingival-buccal side so that neither the main body nor the extension flange is present under said hook in a direction toward the lingual side.

In the present invention according to the first aspect, the width of the extension flange in an occluso-gingival direction is greater than that of the main body in the same direction. Accordingly, it is easy to fix the device to a band. Further, the broad shape of the extension flange has the added advantage that even if dusts during welding flown from the fixed extension flange, they have no potential to block the entrance (exit) of the opening in the main body and there is no likelihood that difficulty is encountered with the passage of a principal wire through the opening.

In the present invention according to the second aspect, the broad extension flange enables the device to be fixed to the band in positions that are away from the area of the opening and displaced toward sites closer to the occlusion and gingival sides. As a result, the possibility of disfigured areas and pressure marks to block the entrance and exit of the opening in the main body is completely eliminated. In the present invention according to the third aspect, the width of the main body is adjusted to the smallest value that ensures the necessary minimum strength. Accordingly, there is a reduced chance for the device to cause occlusive interference with antagonistic teeth on the occlusion side and compress the gingiva on the gingival side. In the present invention according to the fourth aspect, the hook lies on a ridgeline on both the gingival and buccal sides of the main body and extends in a direction toward the gingival-buccal side. Therefore, neither the main body nor the extension flange is present under the hook in a direction toward the lingual side. Hence, there is no chance for the device to contact and compress the gingival and, in addition, the area of the oral cavity under the hook can be easily polished to provide a very good condition in oral hygiene.

BRIEF DESCRIPTION OF THE DRAWINGS

In the accompanying drawings:

FIGS. 7A and 7B show another embodiment according to the present invention;

FIG. 7A is a mesial side view of a buccal tube of this embodiment, and

FIG. 7B is a view of the buccal tube of this embodiment viewed from a upper side; and FIGS. 8A and 8B show still another embodiment according to the present invention;

FIG. 8A is a mesial side view of a buccal tube of this embodiment, and

FIG. 8B is a view of the buccal tube of this embodiment viewed from a upper side.

PREFERRED EMBODIMENTS OF THE INVENTION

The present invention is described below in detail with reference to the preferred embodiments shown in accompanying drawings.

Figure 1A:
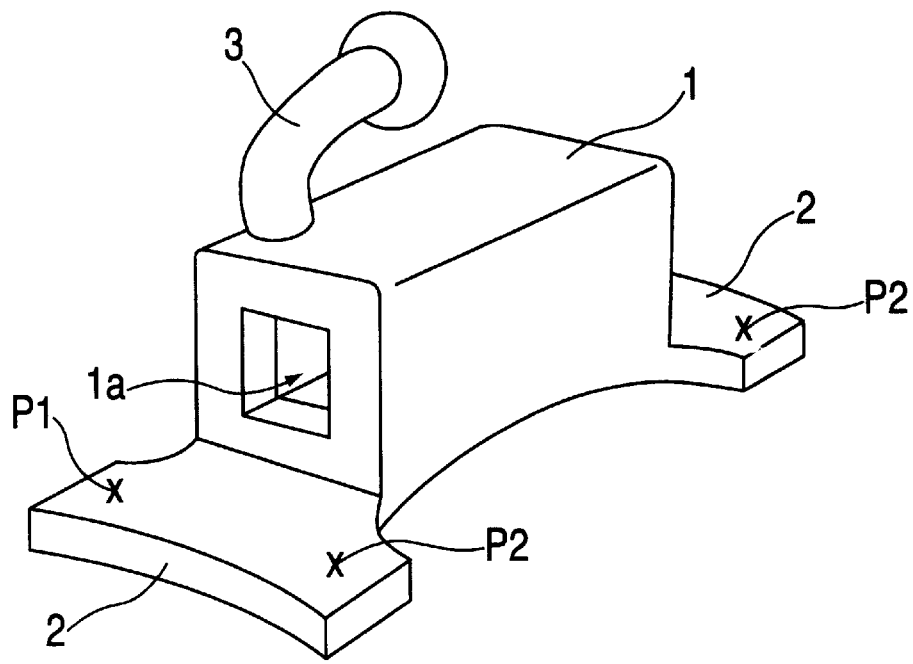
FIG. 1A is a perspective view showing an orthodontic buccal tube according to an embodiment of the invention.
Figure 1B:
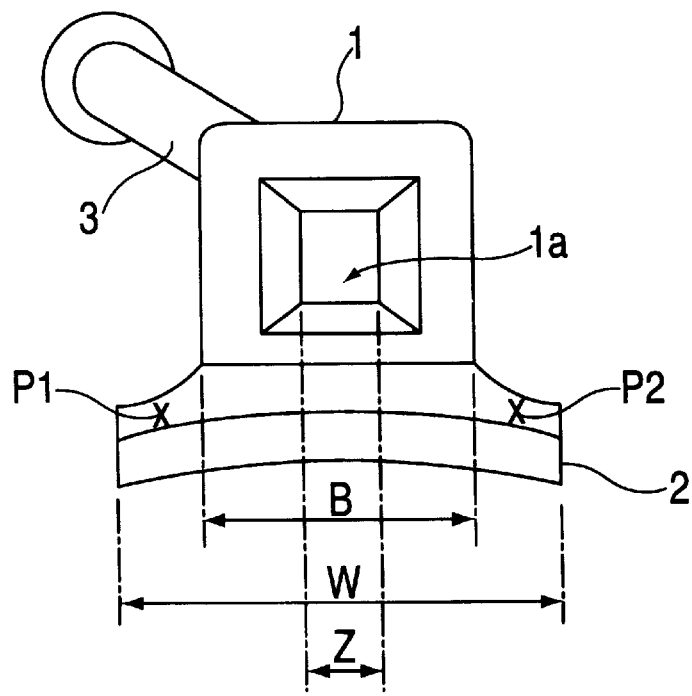
FIG. 1B is a mesial side view of the buccal tube of FIG. 1A.
Figure 1C:
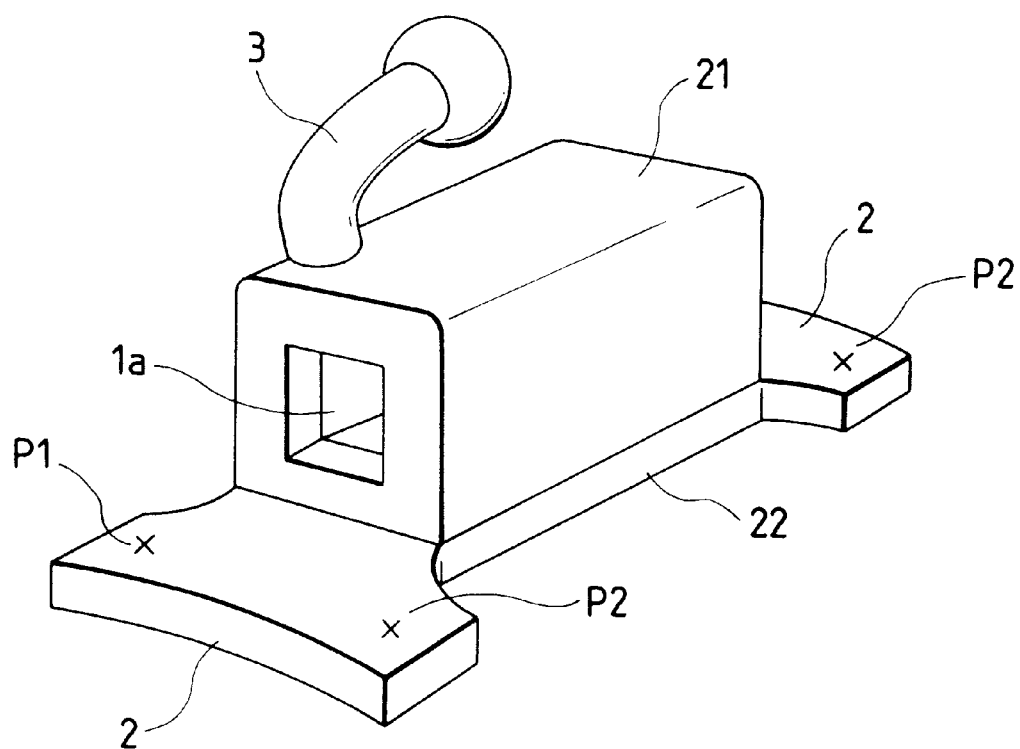
FIG. 1C is a perspective view showing an orthodontic buccal tube according to another embodiment of the invention.
Figure 2A:
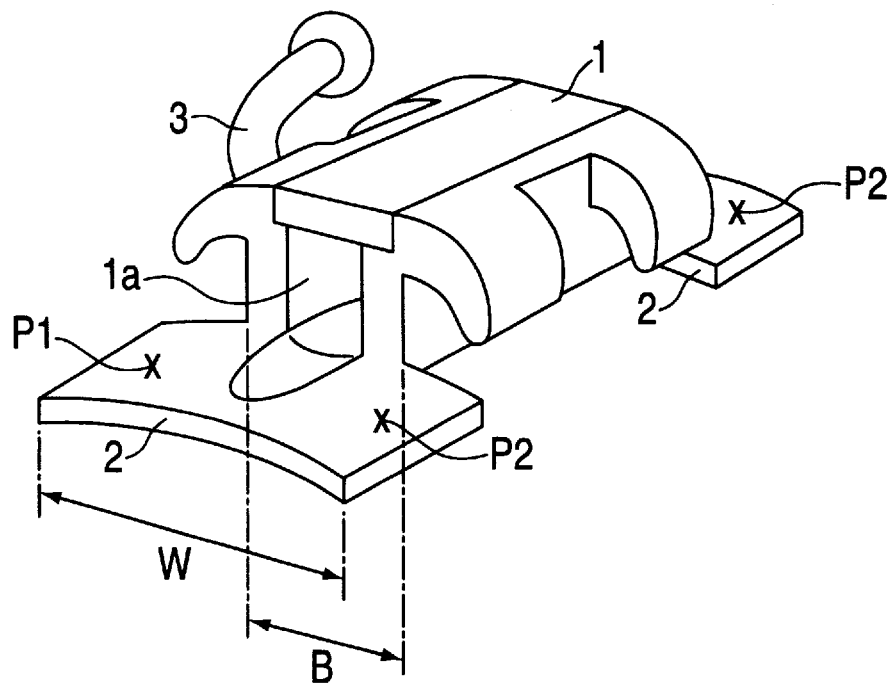
FIG. 2A is a perspective view showing another embodiment of a convertible buccal tube of the invention.

The orthodontic device according to the preferred embodiment of the present invention is a buccal tube of the integral molding type (one-piece type). As shown in FIGS. 1A and 1B, the buccal tube consists of a rectangular tube body 1, a pair of weld flanges 2 and a hook 3. The rectangular tube body 1 has a through-hole 1a serving as an opening through which an end of an arch wire serving as a principal wire is detachably passed in a mesiodistal direction. The pair of weld flanges 2 extend in the mesiodistal direction of the rectangular tube body 1. The hook 3 engages an elastic wire (thread or chain) or a ligature wire. The buccal tube shown in FIGS. 1A, 1B and 1C has the features of the construction described below. Incidentally, as shown in FIG. 2A, the through-hole 1a may be of such a type that a groove becomes exposed upon removal of a convertible cap or other part; and further, the tube body 1 need not be a rectangular tube in a strict sense of the term.

In the embodiment, the width W of each weld flange 2 in an occluso-gingival direction is adjusted to be greater than the width B of the rectangular tube body 1 in the same direction (along the axis of a tooth). The broad weld flange 2 is welded to a band at sites P1 and P2 on the gingival and occlusion sides, respectively, that are distant from the entrance and exit of the through-hole 1a.

At the same time, the hook 3 is formed in such a way that it lies on a ridgeline on both the gingival and buccal sides of the rectangular tube body 1 and extends in a direction toward the gingival-buccal side and that neither the rectangular tube body 1 nor the weld flange 2 is present under the hook 3 in a direction toward the lingual side.

That is, the sites P1 and P2 exists at the outside of the range of Z as shown in FIG. 1B. The length of Z corresponds to the width of the through-hole 1a in the occluso-gingival direction. Preferably, the sites P1 and P2 exists at the outside of the range of B, which is the width of the rectangular tube body 1 in the occluso-gingival direction.

Figure 5:
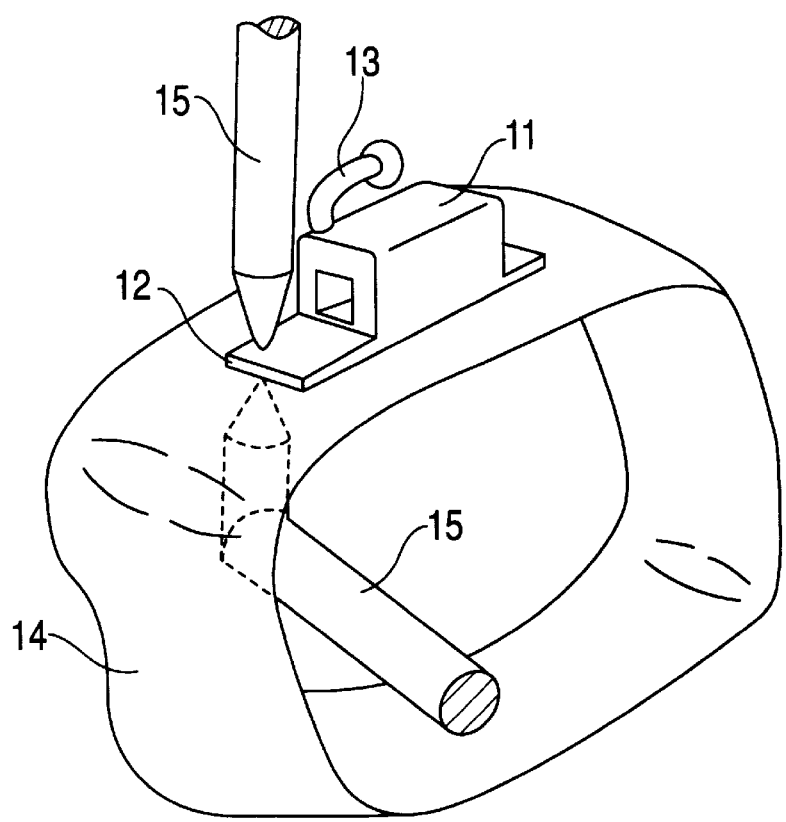
FIG. 5 is an illustration showing how an orthodontic buccal tube is welded to an band.
Figure 6:
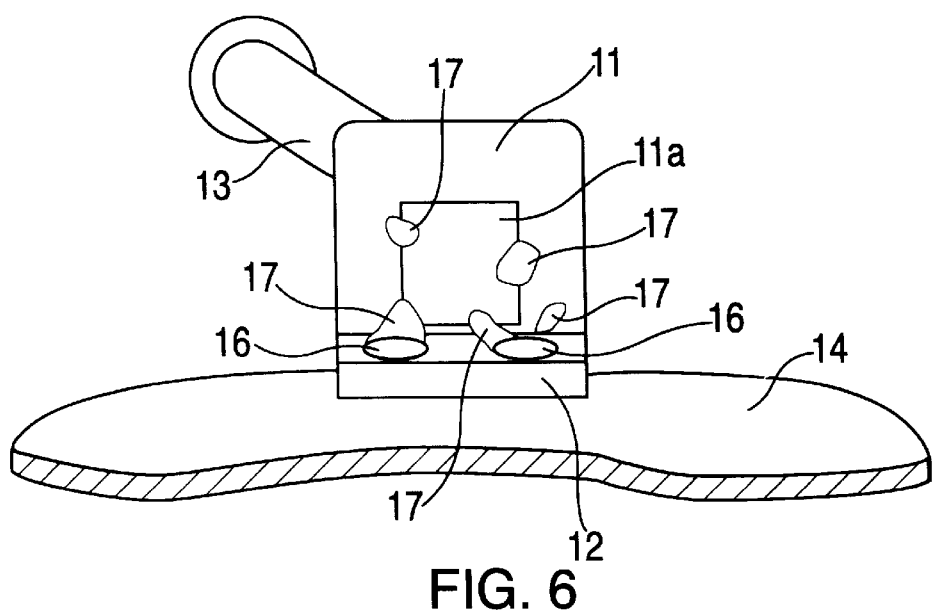
FIG. 6 is a side view showing a through-hole in a rectangular tube body that has been blocked at the entrance and exit.

Because of this construction, the buccal tube of the embodiment under consideration need not be welded to an band (see FIG. 5) at spots very close to the entrance and exit of the through-hole 1a as has been the case in the prior art. Alternatively, the broad shape of the pair of weld flanges 2 is positively utilized such that welding is done at four sites of the flanges distant from the boundary of the through-hole 1a, two of which are at sites P1 on the gingival side and the rest of which are at site P2 on the occlusion side. Even if these welding sites P1 and P2 fuse to become disfigured or splashes or dusts are flown, they will cause no adverse effects on the entrance or exit of the through-hole 1a and there is an assurance for an end of the arch wire to be smoothly passed through the through-hole 1a.

In addition, each of the weld flanges 2 according to the embodiment under consideration is not elongated in a mesiodistal direction as in the conventional art but its width W in an occluso-gingival direction is extended. As a natural consequence, the length of each flange is sufficiently short in a mesiodistal direction that it can easily conform in shape to varying sizes of the band, offering the added advantage that there is no possibility that the band deforms upon welding to present difficulty in assuring good fit to the crowns of molars.

In contrast with the width W of each weld flange 2, the width B of the rectangular tube body 1 is adjusted to the smallest value that assures the necessary minimum strength. Accordingly, there is little likelihood that the device causes either occlusive interference with antagonistic teeth on the occlusion side or compresses the gingival on the gingival side. The small breadth of the rectangular tube body 1 also proves very advantageous if the buccal tube is to be fitted over the second molar that has just erupted, particularly in the case where it is closer to the gingiva. If the buccal tube is fitted over the lower molars, occlusive interference with the upper molars may be a problem but even in this case, the small width of the rectangular tube body 1 contributes to minimize the possible occlusive interference with the upper molars.

In addition, the hook 3 lies on a ridgeline on both the gingival and buccal sides of the rectangular tubular body 1 and extends in a direction toward the gingival-buccal side. Therefore, neither the rectangular tube body 1 nor the weld flange 2 is present under the hook 3 in a direction toward the lingual side. This not only eliminates the chance of the buccal tube of contacting the gingival but also provides ease in brushing the area of the oral cavity under the hook 3 to keep a good condition in oral hygiene.

In the embodiment under consideration, the occlusion and gingival sides of the rectangular tube body 1 form parallel planes, so it can be handled very easily if it is held with tweezers. What is more, the top of the buccal side of the body 1 also forms a plane, so in the case of spot welding the buccal tube to the band temporarily, the upper electrode will not slip, thereby allowing the welding operation to be performed in a simple manner.

In the above embodiment, the rectangular tube body 1 and the weld flanges 2 are integrally formed. However, the present invention can be applied to a buccal tube in which a rectangular tube body 21 are joined with a base 22 having the weld flanges 2 by brazing or laser welding as shown in FIG. 1C. A portion of the base 22, where the rectangular tube body 21 is joined, preferably has a width substantially equal to the width of the rectangular tube body 21.

Figure 2B:
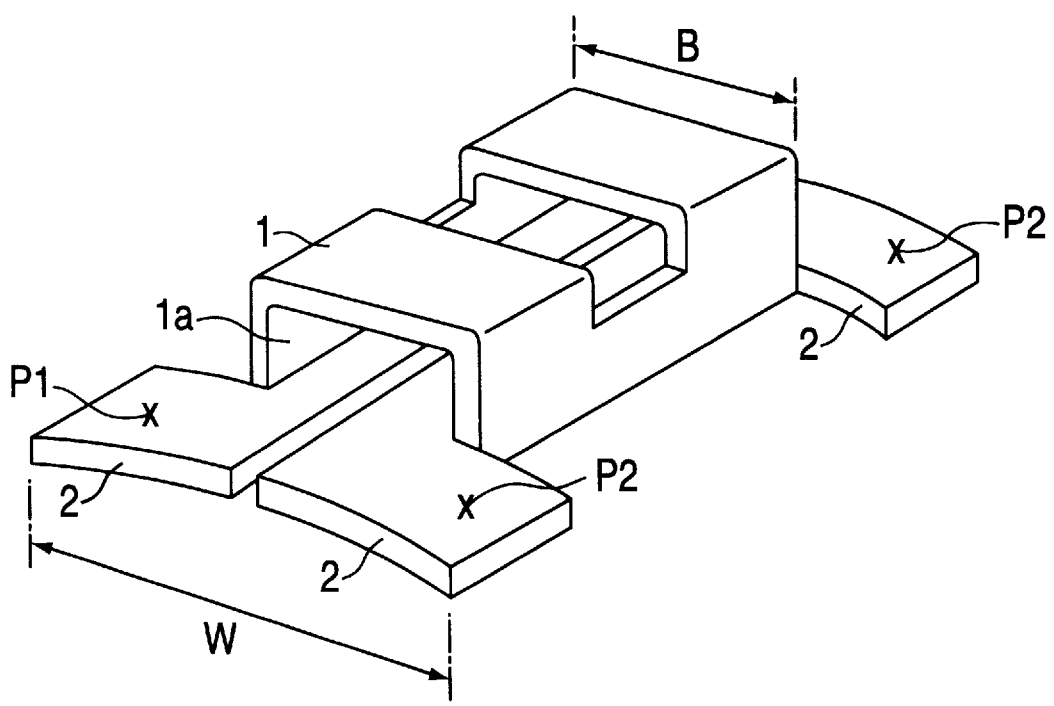
FIG. 2B is a perspective view of lingual sheath showing other embodiment of orthodontic appliance.
Figure 3A:
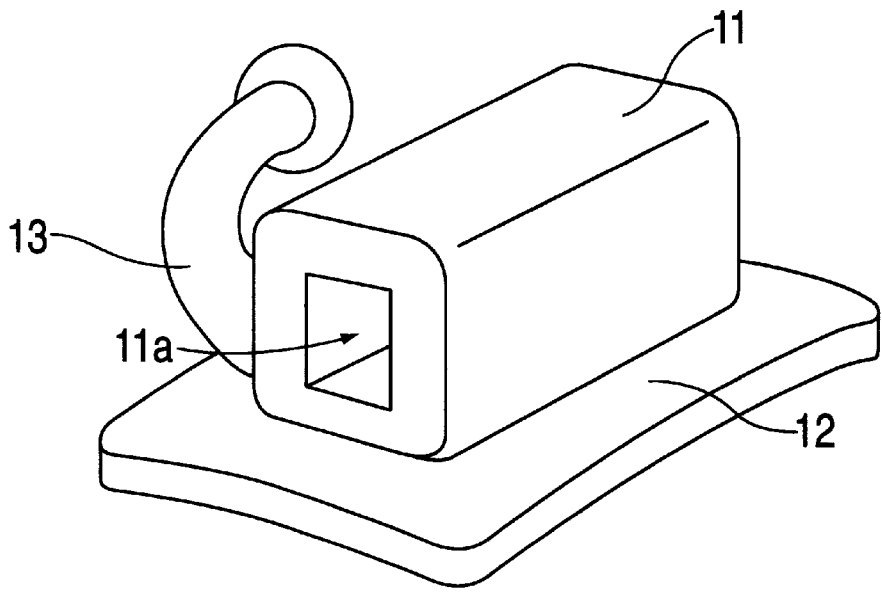
FIG. 3A is a perspective view showing a conventional, separately fabricated orthodontic buccal tube.
Figure 3B:
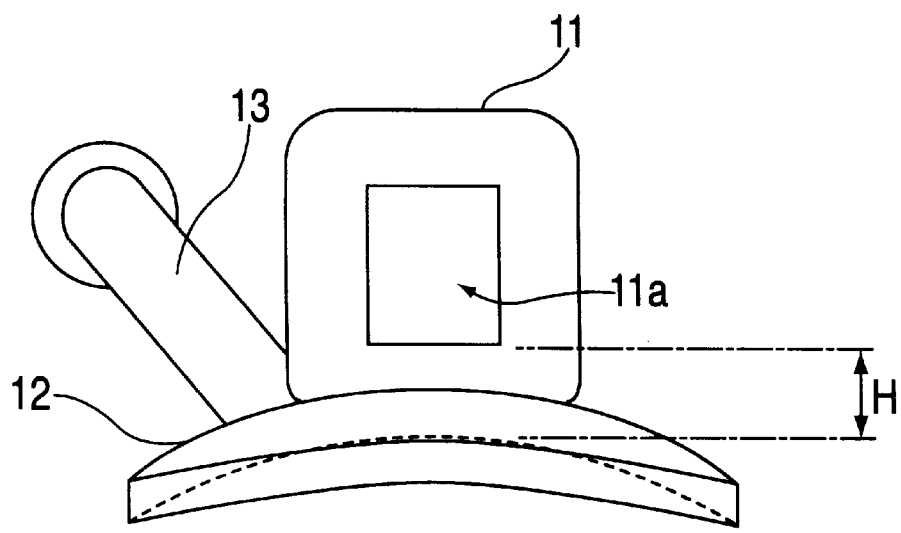
FIG. 3B is a mesial side view of the same buccal tube.
Figure 4A:
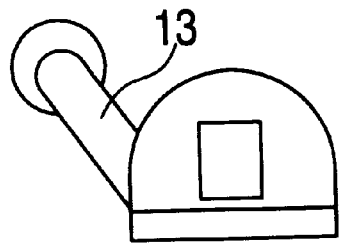
FIG. 4A is a perspective view showing a conventional, integrally molded orthodontic buccal tube.
Figure 4B:
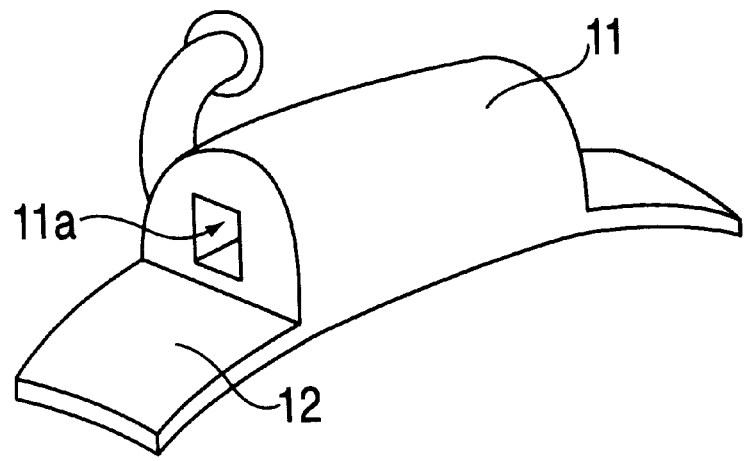
FIG. 4B is a mesial side view of the conventional buccal tube of FIG. 4A.

The foregoing description of the preferred embodiment of the invention assumes a buccal tube of the most common type. However, this is not the sole case of the invention and it may be applied to buccal tubes of other types including a "convertible" buccal tube as shown in FIG. 2A and a lingual attachment, commonly called a "lingual sheath", as shown in FIG. 2B. In addition to the lingual sheath, there is a lingual tube as the lingual attachment. Even in these types of buccal tube, the width W of each weld flange 2 in an occluso-gingival direction is of course adjusted to be greater than the width B of the rectangular tube body 1 in the same direction.

Further embodiments according to the present invention will be described as follows.

FIGS. 7A and 7B show another embodiment according to the present invention. FIG. 7A is a mesial side view of a buccal tube of this embodiment, and FIG. 7B is a view of the buccal tube of this embodiment viewed from a buccal side. The elements similar to those of the embodiment shown in FIGS. 1A and 1B are given the same reference numerals, and their explanations are omitted herein.

In the buccal tube shown in FIGS. 7A and 7B, a through-hole 1b is tipped with respect to an occlusal plane OP. A flange 22 is eccentric toward the gingival side and a flange 23 is eccentric toward the occlusal side. In this embodiment, a rectangular tube body 1 is not tipped, but the through-hole 1b is tipped.

FIG. 8A and 8B show still another embodiment according to the present invention. FIG. 8A is a mesial side view of a buccal tube of this embodiment, and FIG. 8B is a view of the buccal tube of this embodiment viewed from a buccal side. The elements similar to those of the embodiment shown in FIGS. 1A and 1B are given the same reference numerals, and their explanations are omitted herein.

In the buccal tube shown in FIGS. 8A and 8B, both of a through-hole 1c and a rectangular tube body 1 is tipped with respect to an occlusal plane OP. In this embodiment, flanges 24, 25 at the mesial side and the distal side themselves are eccentric.

In the above two embodiments, the opening of the through-hole is eccentric with respect to the buccal tube body and flanges. Further, when it is applied to lower molars, generally, the angle θ between the occlusal plane OP and the through-hole 1b (1C) is 6° at maximum. This is because the uprighting of the lower molars or the anchor effect is clinically expected during the orthodontic treatment of the arch of the lower teeth arrangement.

Incidentally, the structures as shown in FIGS. 7A, 7B, 8A and 8B can be applied to the so-called convertible buccal tube as shown in FIG. 2A.

As described above, the width of the extension flange in an occluso-gingival direction is greater than that of the main body in the same direction. It is possible to fix the orthodontic device of the present invention to a band. The broad shape of the extension flange has the added advantage that even if pressure marks or other disfigured areas bulge from the fixed extension flange, they have no potential to block the entrance or exit of the opening in the main body and there is no likelihood that difficulty is encountered with the passage of a principal wire through the opening.

Further, the broad extension flange enables the orthodontic device of the present invention to be fixed in positions that are away from the area of the opening and displaced toward sites closer to the occlusion and gingival sides. As a result, the possibility of disfigured areas and pressure marks to block the entrance and exit of the opening in the main body is completely eliminated. Further, the width of the main body is adjusted to the smallest value that ensures the necessary minimum strength. Accordingly, there is a reduced chance for the device to cause occlusive interference with antagonistic teeth on the occlusion side and compress the gingival on the gingival side. Moreover, the hook lies on a ridgeline on the both gingival and buccal sides of the main body and extends in a direction toward the gingival-buccal side so that neither the main body nor the extension flange is present under the hook in a direction toward the lingual side. Hence, there is no chance for the device to contact and compress the gingival and, in addition, the area of the oral cavity under the hook can be easily polished to provide a very good condition in oral hygiene.

What is claimed is:

1. An orthodontic device comprising:
   a main body having a base region and a through-hole to which an opening is formed to permit detachable passage of a principal wire; and
   flanges formed at a mesial side and a distal side of said base region, said orthodontic device being fixed via said flanges to a band to be fitted over a tooth;
   wherein a width of said flanges in an occluso-gingival direction is greater than a width of said base region of said main body in the occluso-gingival direction.

2. The orthodontic device according to claim 1, wherein a position where said flanges are fixed to the band is away from said through-hole in the occluso-gingival direction and said position is displaced toward either the occlusion side or the gingival side.

3. The orthodontic device according to claim 1, wherein the width of the main body in an occluso-gingival direction is small enough to avoid occlusive interference with antagonistic teeth on the occlusion side and avoid contact with the gingiva on the gingival side.

4. The orthodontic device according to claim 1, further comprising a hook which lies on both the gingival and buccal sides of the main body and extends in a gingival-buccal direction so that neither the main body nor the flanges are present under said hook in the lingual direction.

5. The orthodontic device according to claim 1, wherein said flanges are formed integral with said main body.

6. The orthodontic device according to claim 1, wherein said orthodontic device is a buccal tube.

7. The orthodontic device according to claim 6, wherein said flanges are fixed to a band to be fitted over a molar or bicuspid.

8. The orthodontic device according to claim 6, wherein a position where said flanges are fixed to the band is away from said through-hole in the occluso-gingival direction and said position is displaced toward either the occlusion side or the gingival side.

9. The orthodontic device according to claim 6, wherein the width of the main body in an occluso-gingival direction is small enough to avoid occlusive interference with antagonistic teeth on the occlusion side and avoid contact with the gingiva on the gingival side.

10. The orthodontic device according to claim 6, further comprising a hook which lies on both the gingival and buccal sides of the main body and extends in a gingival-buccal direction so that neither the main body nor the flanges are present under said hook in the lingual direction.

11. The orthodontic device according to claim 1, wherein said orthodontic device is a lingual attachment provided on a lingual side.

12. The orthodontic device according to claim 11, wherein said flanges are fixed to a band to be fitted over a molar or bicuspid.

13. The orthodontic device according to claim 11, wherein a position where said flanges are fixed to the band is away from said through-hole in the occluso-gingival direction and said position is displaced toward either the occlusion side or the gingival side.

14. The orthodontic device according to claim 11, wherein the width of the main body in an occluso-gingival direction is small enough to avoid occlusive interference with antagonistic teeth on the occlusion side and avoid contact with the gingiva on the gingival side.

15. The orthodontic device according to claim 11, further comprising a hook which lies on both the gingival and lingual sides of the main body and extends in a gingival-lingual direction so that neither the main body nor the flanges are present under said hook in the buccal direction.

16. The orthodontic device according to claim 1, wherein the through-hole is tipped with respect to an occlusal plane, and said flanges comprise a flange eccentric toward a gingival side and a flange eccentric toward an occlusal side.

17. The orthodontic device according to claim 1, wherein the through-hole and said main body are tipped with respect to an occlusal plane, and said flanges comprise a flange eccentric toward a gingival side and a flange eccentric toward an occlusal side.

* * * * *